United States Patent [19]

Kaplan et al.

[11] Patent Number: 4,574,116
[45] Date of Patent: Mar. 4, 1986

[54] METHODS AND CELL LINES FOR IMMORTALIZATION AND MONOCLONAL ANTIBODY PRODUCTION BY ANTIGEN-STIMULATED B-LYMPHOCYTES

[75] Inventors: Henry S. Kaplan, Stanford; Nelson N. H. Teng; Kit S. Lam, both of Palo Alto, all of Calif.; Francisco Calvo-Riera, Leon, Spain

[73] Assignee: The Board of Trustees of the Leland Stanford Jr. University, Stanford, Calif.

[21] Appl. No.: 457,795

[22] Filed: Jan. 13, 1983

[51] Int. Cl.$^4$ .................. C12P 21/00; C12N 15/00; C12N 13/00; C12N 5/00
[52] U.S. Cl. .................. 435/68; 435/172.2; 435/172.3; 435/240; 435/948; 435/173; 935/96; 935/100; 935/106
[58] Field of Search .............. 435/68, 240, 241, 172.2, 435/172.3, 948; 935/56, 34, 32, 71, 90, 93, 100, 96, 106

[56] References Cited

FOREIGN PATENT DOCUMENTS 0057107 8/1982 European Pat. Off. ............ 435/240
2079313 1/1982 United Kingdom ................ 435/948

OTHER PUBLICATIONS

Kozbor et al, "Human Anti Tetanus Toxoid Monoclonal Antibody Secreted by EBV-Transformed Human B Cells Fused with Murine Myeloma", Hybridoma, 1(3), pp. 323-328 (1982).
Croce et al, "Preferential Retention of Human Chromosone 14 in Mouse X Human B Cell Hybrids", European Journal of Immunology 10, pp. 486-488 (1980).
Tucker et al, "Specific Bovine Monoclonal Antibody Produced by a Re-Fused Mouse/Calf Hybridoma", Hybridoma 3(2), pp. 171-176 (1984).
Ostberg et al, "Human X (Mouse X Human) Hybridomas Stably Producing Human Antibodies", Hybridoma 2(4), pp. 361-367 (1983).
Levy et al, "Rescue of Immunoglobulin Secretion from Human Neoplastic Lymphoid Cells by Somatic Cell Hybridization", Proceedings of the National Academy of Sciences, 75(5), pp. 2411-2415 (1978).
Nowinski et al, "Human Monoclonal Antibody Against Forssman Antigen", Science 210, pp. 537-539 (1980).
Olsson et al, "Human Human Hybridomas Producing Monoclonal Antibodies of Predefined Antigenic Specificity", Proceedings of the National Academy of Sciences, 77(9), pp. 5429-5431 (1980).
Shulman et al, "A Better Cell Line for Making Hybridomas Secreting Specific Antibodies",Nature, 276, pp. 269-270 (1978).
Davidson, "Genetics of Cultural Mammalian Cells, as Studied by Somatic Cell Hybridization", National Cancer Institute Monograph, 48, pp. 21-30 (1976).
Southern et al, "Mammalian Cell Transformation with SV40 Hybrid Plasmid Vectors", Eukaryotic Viral Vectors, Cold Spring Harbor Lab, (1981) pp. 41-45.
Littlefield, "Selection of Hybrids from Matings of Fibroblasts in vitro and Their Presumed Recombinants", Science, 145, pp. 709-710 (1964).
Wright, "The Selection of Heterokaryons and Cell Hybrids using the Biochemical Inhibitors Iodoacetamide and Diethylpyrocarbonate", Techniques in Somatic Cell Genetics ed, Shay, Plenum Press, NY, pp. 47-65 (1982).
Fazekas et al, "Production of Monoclonal Antibodies: Strategy and Tactics",Journal of Immunological Methods, 35, pp. 1-21 (1980).

Primary Examiner—Alvin E. Tanenholtz
Assistant Examiner—John Edward Tarcza
Attorney, Agent, or Firm—Bertram I. Rowland

[57] ABSTRACT

Methods are provided for producing fusion partners which involve employing an immortalized human myeloma cell line sensitive to HAT and having an additional dominant selectable resistance marker and fusing the doubly marked human myeloma cells with a stable immortalized rodent myeloma cell line, desirably previously subjected to substantial chromosome damage, and isolating cells having a substantially complete chromosomal complement of the rodent cell and at least about one chromosome of the human cell having a gene expressing said resistance, thereby being resistant to a selective agent. The resulting heteromyeloma may be fused with high efficiency with human lymphocytes to produce monoclonal antibodies.

The cell lines designated as A6 and 36 were deposited at the A.T.C.C. on Jan. 11, 1983 and given accession numbers CRL8192 and CRL8193, respectively.

15 Claims, No Drawings

METHODS AND CELL LINES FOR IMMORTALIZATION AND MONOCLONAL ANTIBODY PRODUCTION BY ANTIGEN-STIMULATED B-LYMPHOCYTES

This invention was made with Government support under Grant No. CA-29876 awarded by the National Institutes of Health. The Government has certain rights in this invention.

BACKGROUND OF THE INVENTION

1. Field of the Invention

For many clinical uses, it is desirable to employ monoclonal antibodies which will not be recognized as foreign by the host. Particularly, where repeated administration of monoclonal antibodies to the host is envisioned, the host is likely to be sensitized and to make antibodies that inactivate xenogeneic monoclonal antibodies and thus vitiate their beneficial effects. Despite the importance of having human monoclonal antibodies available, obtaining such antibodies has proven to be difficult. The human×human crosses occur with relatively low efficiency so that obtaining monoclonal antibodies has proven to be difficult, particularly where the crosses have been with peripheral blood lymphocytes, a convenient source of human B-lymphocytes.

It would therefore be desirable to have malignant fusion partner cell lines capable of being fused at high efficiency with human B-lymphocytes and which do not introduce into the nutrient medium immunoglobulin chains xenogeneic to humans.

2. Description of the Prior Art

EPO 0 044 722 describes a mutant myeloma cell line which, after fusion with antigen-sensitized human spleen B-lymphocytes, yielded monoclonal antibody-secreting human-human hybridomas. Croce et al., *Nature* (1980) 288:488–489 describe a human lymphoblastoid cell line that also yielded antibody-secreting human-human hybridomas. However, the frequency with which such hybridomas are obtained after fusing these and other tested human cell lines with human B-lymphocytes is undesirably low. Many mouse myeloma cell lines are available, some of which, when fused with mouse B-lymphocytes, consistently give a very high yield of mouse antibody-secreting mouse-mouse hybridomas. This suggested that mouse myeloma cell lines could be fused successfully with human B-lymphocytes to generate mouse-human heterohybridomas secreting human monoclonal antibodies. Although such fusions were first reported ten years ago (Schwaber and Cohen, *Nature* (1973) 244:444–447) and have in rare instances yielded stable human monoclonal antibody-producing hybridomas (Schlom et al., *PNAS USA* (1980) 77:6841–6845), this approach has suffered from the fact that human chromosomes are selectively and usually totally eliminated from human-mouse hybrids, thus leading, after a variable but usually brief time interval, to the loss of those human chromosomes (#2, 14, and 22) on which reside the genes for the heavy and light chains of immunoglobulin (the generic class of molecule to which all antibodies belong), and thus to the cessation of human monoclonal antibody production. It is thus clear that the development of methods and cell lines whereby these and other essential human chromosomes are retained in mouse-human heterohybridomas would make this a practical and efficient approach to human monoclonal antibody production.

SUMMARY OF THE INVENTION

Novel methods and cell lines are provided for the efficient production of human monoclonal antibodies. An immortalized human myeloma cell line is modified by introducing a selectable dominant resistance marker, to provide a HAT-sensitive, selectable agent resistant, immortalized human cell line which, when fused with a HAT-sensitive immortalized mouse (or rat) myeloma cell line, particularly after the latter has been treated with chromosome-damaging agents such as x-rays, and then incubated in the presence of the appropriate selection agents, will provide a high yield of viable mouse-human heteromyelomas in which one or more human chromosomes are stably retained. After cloning the most rapidly growing hybrid myeloma cells, the resulting HAT-sensitive hybrid cells may be used for fusing with antigen-sensitized human B-lymphocytes for the stable production of human monoclonal antibodies.

DESCRIPTION OF SPECIFIC EMBODIMENTS

The subject invention concerns novel myeloma cell fusion partners, methods for preparing such myeloma cell fusion partners, intermediates employed for their preparation, and the products obtained using such cell line.

The myeloma cell fusion partners of the subject invention are characterized by being an immortal cell line having a major complement of chromosomes from a lower order mammal, particularly lagomorph or rodent, more particularly rodent, preferably mouse. The cell is a hybrid cell, but is derived from a lower order mammalian myeloma cell ("recipient cell"), initially capable of secretion of antibodies. The cell will be selected as a mutant substantially incapable of expressing any of the fragments involved in the assembly of its own immunoglobulins. Therefore, the subject fusion partner cell will lack the capability to express its own light and heavy chains of immunoglobulins, but will retain the ability to support the secretion into the extracellular fluids of desired specific immunoglobulin (antibody) molecules synthesized from the activated genes of a human B-lymphocyte fusion partner resulting in the processing, assembly and secretion of the mature human immunoglobulin.

The fusion partner cell will contain at least one, and preferably several (2 or more, preferably 5 or more, usually not more than about 20) human chromosomes from a human myeloma cell ("donor cell"). Integrated on one or more of the chromosomes will be a gene providing a selectable dominant resistance marker.

The selectable marker may be any convenient marker which allows for selection of mammalian cells containing the gene and, preferably, a marker which is not likely to be encountered in mammalian cells, nor one which might result from reversion of a mutant. Therefore, while a complementation marker could be employed with an auxotrophic host to provide prototrophy, for the most part, resistance genes to cytocidal agents will be employed, particularly genes providing resistance to cytotoxic antibiotics. Illustrative antibiotics for which resistance can be imparted to a mammalian cell include G-418. The cell will also be sensitive to HAT, which can readily be achieved by conventional techniques. The subject cells are capable of fusion with human B-lymphocytes at high efficiency, providing a greater than 90% yield of heterohybridomas with human B-lymphocytes from lymph nodes, spleens (splenocytes) and peripheral blood, as well as such cells transformed with Epstein-Barr virus.

The subject cells which contain a major complement of the chromosomes of the rodent myeloma and at least one, and preferably more than one human chromosome, having the properties described above, will be hereafter referred to as "heteromyelomas".

It should be understood, that while the heteromyelomas of this invention are primarily concerned with human monoclonal antibodies, heteromyelomas capable of fusing with lymphocytes of other higher mammals may be capable of production in substantially the same way, particularly where one wishes to produce monoclonal antibodies specific for domestic animals and other primates. Thus, the heteromyeloma, rather than having a portion of the human genome, could have a portion of the genome of such other species as domestic animals, e.g. bovine, equine, porcine, canine, feline, etc. or primates, such as monkeys, gorillas, baboons, etc. Thus, the subject invention is not limited to human monoclonal antibodies, but is likely to find its most extensive utilization in the production of human monoclonal antibodies. Therefore, hereafter when referring to human cells, these will be illustrative of higher mammalian cells generally.

In preparing the heteromyeloma, one will employ a human immortalized cell, desirably a myeloma, for fusion with the immortalized mouse (or rat) myeloma. This human chromosomal donor cell is characterized by having two selective markers, first, HAT sensitivity and secondly, a selectable dominant marker. The donor cell will also be sensitive to a cytotoxic agent, which allows for selection against the donor cell in relation to the recipient cell. The dominant selective marker introduced in vitro, becomes integrated on one or more donor cell chromosomes and thus stably maintained in the host cell. The chromosome(s) bearing the dominant selective marker will be capable of transfer to the recipient cell after cell fusion, and of stable maintenance in the resulting heteromyeloma cell in the appropriate selection medium. The chromosome(s) bearing the marker will also be capable of maintenance in the hybridoma resulting from the fusion of the heteromyeloma with the human B-lymphocyte. Moreover, the stable retention in the hybridoma of at least three essential chromosomes from the human B-lymphocyte will be favored by fusion with such heteromyelomas.

The human myeloma donor cell will be significantly more sensitive than the mouse (or rat) cell to killing by an additive which can be introduced into the nutrient medium. A convenient additive is ouabain. Thus, following fusion of the donor human cell with the recipient mouse (or rat) myeloma cell, incubation in the presence of both selection agents (for example, G-418 and ouabain) will be cytocidal for the unfused donor and recipient cells, but not for the heteromyeloma.

Various human myeloma cells may be employed for modification with the selective marker. U-266 described by Nilsson et al., *Clin. Exp. Immunol.* (1970) 7:477–489 is illustrative. HAT-sensitive mutants of these myeloma cells may be selected by conventional methods, such as, for example, incubation in the presence of 8-azaguanine or 6-thioguanine at successively increased concentrations. Introduction of DNA bearing the selectable dominant resistance marker gene may be done by any conventional technique, such as transformation or transfection. Various vectors are available which can be replicated in mammalian host cells. Conveniently, recombinant vectors derived from the introduction into plasmids or bacterial viruses of genetic elements derived from mammalian viruses, such as simian virus 40, papilloma virus or other competent replication system may be employed. Included in the recombinant vector will be a dominant gene providing for selection of the cells in which the marker is expressed; for example, expression of a gene for resistance to a cytotoxic antibiotic would permit cells bearing the marker to survive when incubated in that antibiotic, whereas those cells without the marker would be killed. Illustrative of such markers is the gene for neomycin resistance, which imparts resistance to the antibiotic G-418 (available from Schering Corp.) to the host mammalian cells. By having dual selective markers, one of the markers being sensitivity, the other marker being resistance, one can kill the donor cells by virtue of the sensitivity of the donor cells to a selective agent, e.g. ouabain, thus allowing for selection for the heteromyeloma.

The other parent cell, the mouse (or rat) myeloma recipient cell, may be any mammalian cell of lower order, which has the following desired properties. The cell must be an immortalized myeloma cell, capable of receiving at least one human chromosome and stably maintaining at least one human chromosome and be capable of fusion with a B-lymphocyte to provide a stable hybridoma. In addition, the recipient parent should be substantially non-secreting of its own immunoglobulins or fragments thereof, but be capable of secreting human immunoglobulins, when the genes expressing the precursors to the immunoglobulins are received by the heteromyeloma from a human B-lymphocyte. Thus, the recipient parent must be capable of processing and assembling the immunoglobulin component chains and secreting the mature human immunoglobulin.

The recipient parent should be sensitive to the cytotoxic agent to which resistance has been imparted to the donor parent cell. Thus, where neomycin resistance is imparted to the donor parent cell, the recipient parent cell should be G-418-sensitive. Therefore, heteromyelomas which receive the marker gene (neo$^r$) will be able to survive in a medium which contains factors lethal to the two parents. The recipient cells should also be HAT-sensitive or have some other sensitivity which will allow for selection of hybridomas.

While mouse cells are not essential to the subject invention, the fact is that mouse cells have found the widest use, and a number of stable HAT-sensitive myeloma fusion partner cell lines are available. Among such fusion partners are P3-X63 Ag8; P3X63-Ag 8.653-NP; P3-NSI-1-Ag4-1; MPC11-X45-6tg; BW5147; and EL-4 (Melchers et al., *Current Topics in Microbiology and Immunology: Lymphocyte Hybridomas*, Vol. 81, Springer-Verlag, Berlin, 1978, p. X. (The cell of particular interest is P3X63-Ag 8.653-NP.)

It is found that better results are obtained where the recipient parent cells are exposed to chromosome-damaging agent, such as x-rays. By irradiating the chromosomes of the recipient parent cells, those chromosomes bearing damaged genes of the recipient parent cells may be complemented by chromosomes from the donor parent cells. It is found that the irradiated recipient parent can retain a higher number of donor chromosomes than when the recipient parent has not been subjected to irradiation. Any convenient technique for inducing chromosome damage may be employed, such as x- or gamma irradiation, or exposure to chemical mutagens, e.g. ethyl methane sulfonate or other alkylating agent. Desirably, x- or gamma irradiation is employed, since this chromosome-damaging agent is likely to yield deletions, rather than point mutations, as with some chemical mutagens, thus excluding spontaneous reversion and favoring complementation of the deleted gene(s) by the retention of donor cell chromosomes.

The donor parent may be prepared by selecting a stable myeloma line, preferably non-secreting although this property may be attained during processing, and introducing a selectable marker into the human donor cell. As already indicated, the modification of the human donor parent cell can be by conventional ways, for example, transfection. A shuttle vector may be employed having competent replication systems for both the donor parent cell and a prokaryote. As illustrative, one may prepare protoplasts of transformed prokaryotes, containing the shuttle vector having the selective marker, which protoplasts are combined with the donor parent cells under fusing conditions and the cells grown in appropriate nutrient media under selective conditions. Desirably, the fastest growing cells are selected and cloned as donor parent cells.

The recipient cells may be any one of a number of available mouse myeloma cells or may be developed independently, if desired. As already indicated, the recipient parent should either not secrete immunoglobulins or should lose its capability to secrete isogenic immunoglobulins upon receiving the chromosomes from the donor parent.

The heteromyeloma may be readily prepared by fusion of the two parents under conventional fusion conditions. See for example, Oi and Herzenberg, in Selected Methods in Cellular Immunology, B. Mishell and S. Shiigi eds., W. H. Freeman, San Francisco, 1979, pp. 351-372. The two parent cells are mixed and an appropriate fusion medium containing a non-ionic detergent fusogen, particularly polyethylene glycol of molecular weight 1000-6000 (usually 1500-4000) daltons, is added. The period for the fusion is generally less than 2 min. (usually 1 min.) and the resulting cells are then gently but rapidly washed free of the non-ionic detergent. The individual parental cells will usually be present in from about $10^6$–$10^8$ cells/ml.

The cells are then seeded at relatively high concentrations in the wells of cell culture plates in nutrient medium (usually RPMI-1640+15% fetal calf serum), at about $10^4$–$10^6$ (optimally 2–3×$10^5$) cells per well, and after sufficient time for recovery from the fusion, generally 1–4 days, the cells are then selected by incubation in selective medium. The selective medium will contain agents known to be lethal to the two parent cells, but not to the heteromyeloma. While normally resistant hybrids will grow out in about 1–2 weeks, it is desirable that the culture be expanded in the selective medium for about 3–4 weeks, with the selective medium being repeatedly refreshed.

Surviving cells may then be selected and cloned based on their growth patterns. Their utility for use as a fusion partner may then be tested by performing fusions in conventional ways with antigensensitized or activated human B-lymphocytes or lymphoblastoid cell lines and measuring the fusion efficiency and, as appropriate monoclonal antibody production.

The following examples are offered by way of illustration and not by way of limitation.

EXPERIMENTAL

In the present examples, the source of the human myeloma cell line was mycoplasma-infected. Therefore, the details for curing the cells from mycoplasma will be provided, although it should be understood that where mycoplasma-free donor myeloma cells are available, these would be the cells of choice.

One ampule of U-266 (K. Nilsson, Uppsala, Sweden) known to be mycoplasma-infected was tested for viability by trypan blue exclusion, showing 42% viability, total viable cells equal 3.5×$10^6$. The cells were suspended in 10 ml RPMI-1640 in a 25 cc flask. The whole flask was centrifuged, the medium replaced with 10 ml fresh Iscove's medium and the cells placed on a Ficoll-Hypaque gradient. Live cells were seeded in one well of a 24-well cluster plate, followed by expansion to two wells. The cells were then transferred to a 25 cc flask, half of the medium replaced with fresh Iscove's medium three days later, followed by replacing two-thirds of the medium five days later and followed by replacing four-fifths of the medium five days later.

The mycoplasma infection was eradicated as follows: Five ml of U-266 cells in Iscove's medium were heated in a water bath at 41° C. for 44 hours. The cells were then washed 1x with PBS, followed by incubation for one hour with Pronase at 37° C., followed by sedimentation on a Ficoll-Hypaque gradient. The cells were then washed 3× with PBS, yielding 29×$10^4$ total viable cells. Of these, 69 μl ($10^4$ cells) were suspended in 10 ml Iscove's medium and seeded at 100 μl/well (~100 cells/well) in a 96-well microtiter plate. The cells which had been incubated at 41° C. for 44 hours were shown to be negative for mycoplasma in three successive tests by the Hoechst 33258 method, and later also by the broth culture and fluorescent antibody methods. This cell line was designated as FU-266.

FU-266 cells were selected in RPMI-1640 in the presence of 20 μg/ml of 8-azaguanine or 10 μg/ml of 6-thioguanine. The latter cells grew well and were tested and shown to be HAT-sensitive and were used in the subsequent fusion as the donor parent.

Transfection of FU-266 was achieved as follows: The transfecting agent was pSV-2 neo$^r$, a recombinant plasmid vector containing the SV40 origin and promoter regions and the *E. coli* gene for neomycin resistance, which also provides G-418 resistance. The recombinant plasmid is described by Berg, *Bioscience Rep.* (1981) 1:269-287. Protoplasts of *E. coli* carrying pSV-2 neo$^r$ were prepared as described by Shaffner, *PNAS USA* (1980) 77:2163-2167, except for resuspension in: MEM+10% sucrose, 10 mM MgCl$_2$, 7% DMSO, and 0.2 μg/ml DNAse I. The optimal concentration of FU-266 cells was 2×$10^6$ cell/well. Resuspension of the protoplast was performed carefully and slowly with a "Vortex" tube in one hand and resuspension medium added drop by drop with the other hand at about 1 ml/min. The protoplast was then allowed to remain at room temperature for 10–30 min. while the FU-266 cells were centrifuged, then resuspended in 12 ml MEM+10% DMSO at 32° C. and 2 ml aliquots added to each well of a 6-well Costar plate, which was then covered with Parafilm and centrifuged 5 min. at 2000 RPM. The supernatant was then aspirated from each well and replaced with 2 ml of the protoplast preparation. The plate was then covered with Parafilm and spun 8 min. at 1500xg with brake setting at 5. The supernatant was again aspirated, and aspirated again after 30 sec. To the mixture of cells is then added polyethylene glycol: 1 ml/well of 50% PEG 1500+10% DMSO at 32° C. for no more than one minute, at which time the PEG solution is aspirated and replaced with 2 ml/well of MEM+10% DMSO. This solution is aspirated and each well washed 3x with MEM. To each well is then added 2 ml/well of Iscove's medium+15% FCS+100 μg/ml gentamycin and the cells incubated overnight. The cells are then loosened and resuspended with a Pasteur pipette.

The transfected FU-266 pSV-2 neo$^r$ cells were seeded into cluster wells and incubated in Iscove's medium+600 μg/ml G-418. After about 10-14 days, large, healthy, viable cell foci were seen in several of the wells containing transfected FU-266 cells. A total of 68 colonies were obtained from $6.142 \times 10^6$ transfected cells plated for a transfection efficiency of $1.1 \times 10^{-5}$. One of these clones, E-1, was selected for further study.

The clone E-1 was grown in RPMI-1640+600 μg/ml G-418+100 mM HEPES buffer, pH 7.3 (filtered through a 0.22μ Millipore filter).

The FU-266 (pSV-2 neo$^r$, HAT$^s$) E-1 clone was fused with the mouse myeloma line P3X63-Ag 8.653-NP (Kearny et al., J. Immunol. (1979) 123:1548) and with the same mouse myeloma line which had been irradiated with 500 rad of $^{137}$Cs gamma rays, using a Mark I, Model 30, $^{137}$Cs irradiator, at a cell concentration about $10^7$ cells/ml in PBS. The fusions were performed according to the method of Oi and Herzenberg, supra, with minor modifications, such as the use of Ca$^{++}$-free Joklik's medium, pH 8.2. The cells were then incubated in Iscove's medium+600 μg/ml G-418 and about $1-5\times10^{-7}$M ouabain. The viable cells were then expanded and in the case of the non-irradiated mouse myeloma line, about 30 clones were obtained and two heteromyelomas selected for further study were designated A-6 and A-10. In the case of the irradiated mouse myeloma lines two fast growing lines were selected for further study and designated #3 and #36.

The heteromyelomas were fused with pokeweed mitogen stimulated peripheral blood lymphocytes by the method of Oi and Herzenberg, supra, with minor modifications and the number and percent of viable clones determined. The following are the results of one such fusion.

| Malignant Fusion Partner Cell | Viable Hybrids Total Wells Seeded | % Viable Hybrids |
|---|---|---|
| A-6 Heteromyeloma | 70/108 | 65 |
| A-10 Heteromyeloma | 9/100 | 9 |
| #3 Heteromyeloma | 37/100 | 37 |
| #36 Heteromyeloma | 107/100 | 97 |
| P3X63-Ag 8.653 Parental Mouse Myeloma | 30/96 | 31* |

*many clones subsequently died out

As evidenced by the above results, the heteromyelomas vary in their efficiency of fusion. One therefore performs the process of the subject invention and screens for the optimal heteromyeloma cell line.

The heteromyeloma clone #36 has given consistently high yields of viable hybridomas; a yield exceeding 100% (an average of more than one hybrid clone per well in all wells) has occurred in some fusions with normal PBL and with a human lymphoblastoid cell line. A high proportion of these hybridomas, ranging up to 100%, were shown by ELISA assays to be secreting the human immunoglobulins IgM or Igb. The clone A-6 was the next best heteromyeloma. One hybridoma resulting from a cross between A-6 and an anti-tetanus toxoid antibody-producing human lymphoblastoid cell line, C-10, has secreted specific IgM(κ) human monoclonal antibody to tetanus toxoid for over six months.

The clones from the non-irradiated mouse myeloma line were shown to retain from about 1-2 human chromosomes per hybrid clone. Upon fusion with a human lymphocyte, the resulting hybridomas were found to contain about 5-6 human chromosomes. With the irradiated mouse myeloma line, the heteromyelomas contained about 3-10 human chromosomes and from 50-100 mouse chromosomes (model number of myeloma line is 57).

The heteromyelomas of the subject invention provide efficient and stable fusion partners for fusion with antigen-sensitized human B-lymphocytes for the stable production of human monoclonal antibodies for long periods of time. The heteromyelomas of the invention are non-secreting prior to fusion, so that the hybridomas secrete only the human monoclonal antibodies produced by the human B-lymphocyte. In addition, it is possible that the resulting hybridomas employing the heteromyelomas can be used with lower mammals to produce ascites fluid. Desirably, the host will have an impaired immune system, e.g. nude mice, so that the hybridoma cells will not be rejected before they secrete significant quantities of human antibody.

In accordance with the subject invention, novel methods and cell lines are provided for the stable production of higher mammalian, particularly human, monoclonal antibodies. High efficiency of transformation is achieved, so that the probability of obtaining stable heteromyelomas retaining one or more human chromosomes is greatly enhanced. The hybridomas resulting from fusion of the heteromyelomas with antigen-sensitized human B-lymphocytes can be stably maintained in vitro for long periods of time, and provide for sustained secretion of the desired human monoclonal antibodies in satisfactory yield in the absence of secreted immunoglobulins or their fragments from the heteromyeloma.

A method is also provided for enhancing the stability of foreign chromosomes from other higher mammalian species, where desirable.

Although the foregoing invention has been described in some detail by way of illustration and example for purposes of clarity of understanding, it will be obvious that certain changes and modifications may be practiced within the scope of the appended claims.

1. A method for producing a heteromyeloma comprising:

fusing in a fusing medium (a) first human myeloma donor cells, which cells are sensitive to a first selective means and have a gene providing resistance to a second selective means originating from said gene being introduced into said donor cells in vitro with (b) rodent recipient myeloma cells capable of stable maintenance in vitro without significant secretion of their own immunoglobulin proteins and significantly less sensitive than said donor cells to said first selective means but sensitive to the second selective means to which said gene provides resistance, to provide a mixture of cells including recipient cells having at least one donor chromosome containing said resistance gene;

growing said mixture of cells under selective conditions for sensitivity to said first and second selective means; and isolating heteromyelomas comprising recipient cells having at least one chromosome of said donor cells bearing said gene.

2. A method according to claim 1, wherein said donor and recipient cells are HAT-sensitive and said recipient cells irradiated or otherwise treated prior to fusing so as to introduce significant damage to one or more essential chromosomes, wherein said recipient cells can retain a higher number of donor chromosomes as compared to undamaged cells.

3. A method according to claim 2, wherein at least one of said selective means is a cytocidal drug.

4. A method according to claim 2, wherein said first selective means is sensitivity to ouabain.

5. A method according to any of claims 1, 2, 3 or 4, wherein said rodent cells are mouse cells.

6. A hybridoma prepared by fusing a heteromyeloma produced according to the method of claim 1 with an activated B-lymphocyte or EBV transformed B-lymphocyte.

7. A method for producing a heteromyeloma of human and mouse cells comprising fusing in a polyethylene glycol containing fusing medium (a) human myeloma cells which are sensitive to HAT and have a gene providing resistance to G-418 as a result of introduction of said gene in vitro with (b) mouse HAT-sensitive myeloma cells capable of stable maintenance in vitro without secretion of mouse immunoglobulins and sensitive to G-418 to provide heteromyeloma cells containing a major complement of mouse chromosomes and at least one human chromosome bearing said gene;

growing said mixture of cells in the presence of ouabain and G-418, whereby only heteromyeloma cells, which are HAT-sensitive, survive; and isolating and cloning said human-mouse heteromyelomas.

8. A heteromyeloma cell derived from a recipient rodent myeloma cell and a donor human myeloma cell, comprising a cell having at least a substantially complete rodent genome, and at least one chromosome from a human cell carrying a gene originating from in vitro introduction imparting resistance to a selective means to which said rodent myeloma cell is sensitive.

9. A heteromyeloma cell according to claim 8, wherein said rodent myeloma cell is a mouse cell.

10. A heteromyeloma according to claim 8, wherein the genome of said rodent myeloma cell has sustained significant chromosome damage originating from exposure to ionizing radiation or radiomimetic chemical agents, wherein said cell can retain a higher number of donor chromosomes as compared to undamaged cells.

11. A heteromyeloma according to any of claims 8, 9 or 10, wherein said rodent cell is the mouse myeloma line P3X63-Ag 8.653-NP and said human chromosome is a human chromosome from mutant human myeloma cell line U-266.

12. A heteromyeloma according to any of claims 8, 9 or 10, wherein said gene imparts resistance to G-418.

13. A hybridoma prepared by fusing a heteromyeloma according to claim 8 with an activated B-lymphocyte or EBV transformed B-lymphocyte.

14. A method for producing human monoclonal antibodies which comprises:

fusing a heteromyeloma having at least one chromosome from a human myeloma cell in a fusing medium with a lymphocyte from a human; and selecting for hybridomas secreting the desired human monoclonal antibodies.

15. A method according to claim 14, wherein said heteromyeloma is derived from mouse myeloma recipient cells.

* * * * *